(12) United States Patent
Walkden (10) Patent No.: US 12,251,514 B2
(45) Date of Patent: Mar. 18, 2025

(54) AIRWAY DEVICE

(71) Applicant: BLUE BEAN MEDICAL LIMITED, Lancashire (GB)

(72) Inventor: Carl Michael Walkden, Lancashire (GB)

(73) Assignee: BLUE BEAN MEDICAL LIMITED, Lancashire (GB)

( * ) Notice: Subject to any disclaimer, the term of this patent is extended or adjusted under 35 U.S.C. 154(b) by 751 days.

(21) Appl. No.: 17/263,682

(22) PCT Filed: Jun. 27, 2019

(86) PCT No.: PCT/GB2019/051822
§ 371 (c)(1),
(2) Date: Jan. 27, 2021

(87) PCT Pub. No.: WO2020/025921
PCT Pub. Date: Feb. 6, 2020

(65) Prior Publication Data
US 2021/0220596 A1    Jul. 22, 2021

(30) Foreign Application Priority Data

Aug. 1, 2018 (GB) ...................................... 1812562

(51) Int. Cl.
*A61M 16/06* (2006.01)
*A61M 16/04* (2006.01)

(52) U.S. Cl.
CPC .... *A61M 16/0616* (2014.02); *A61M 16/0409* (2014.02); *A61M 2210/065* (2013.01)

(58) Field of Classification Search
CPC .......... A61M 16/0616; A61M 16/0409; A61M 2210/065; A61M 16/0418; A61M 16/04; A61M 16/0402
See application file for complete search history.

(56) References Cited

U.S. PATENT DOCUMENTS 7,546,838 B2   6/2009 Lin
7,997,274 B2   8/2011 Baska
(Continued)

FOREIGN PATENT DOCUMENTS

CN   1771067 A   5/2006
CN   205019550 U  2/2016
(Continued)

OTHER PUBLICATIONS

GB Search Report, UK Intellectual Property Office, App. No. GB1812562.5, Jan. 24, 2019, 3 pages.
(Continued)

*Primary Examiner* — Rachel T Sippel
*Assistant Examiner* — Matthew R Moon
(74) *Attorney, Agent, or Firm* — Taft Stettinius & Hollister LLP; Stephen F. Rost (57) ABSTRACT

A laryngeal mask includes a housing having a neck part and a head part extending from a first end of the neck part. The head part further includes a sealing face and an opposing face, the sealing face and the opposing face being connected by an enclosing wall extending upwardly from the sealing face. The sealing face has a peripheral seal for forming a seal around a larynx and having an opening arranged to be positioned over a laryngeal opening. An airway tube is positioned within the housing and extends from a second end of the neck part to the opening in the peripheral seal, wherein the head part includes a resiliently deformable portion positioned between the sealing face and the opposing face. The resiliently deformable portion is a deformable portion of the head part. The resiliently deformable portion has a protrusion and protrudes upwardly from the opposing face.

15 Claims, 9 Drawing Sheets

(56) References Cited

U.S. PATENT DOCUMENTS

| | | | |
|---|---|---|---|
| 8,413,658 B2* | 4/2013 | Williams | A61M 16/085 |
| | | | 128/207.14 |
| 8,434,488 B2* | 5/2013 | Li | A61M 16/0443 |
| | | | 128/207.15 |
| 8,714,159 B2 | 5/2014 | Baska | |
| 9,265,904 B2* | 2/2016 | Esnouf | A61M 16/04 |
| 2006/0027238 A1 | 2/2006 | Lin | |
| 2006/0180156 A1 | 8/2006 | Baska | |
| 2013/0092172 A1* | 4/2013 | Nasir | A61M 16/0431 |
| | | | 128/207.15 |
| 2014/0000624 A1* | 1/2014 | Miller | A61M 16/04 |
| | | | 128/207.15 |
| 2017/0216544 A1* | 8/2017 | Baska | A61M 16/0452 |
| 2021/0220596 A1 | 7/2021 | Walkden et al. | |

FOREIGN PATENT DOCUMENTS

| | | |
|---|---|---|
| DE | 102015103155 A1 | 1/2016 |
| EP | 3829683 A1 | 6/2021 |
| GB | 2445655 A | 6/2011 |
| WO | 2005011784 A1 | 2/2005 |
| WO | 2015015233 A1 | 2/2015 |
| WO | 2020025921 A1 | 2/2020 |

OTHER PUBLICATIONS

International Search Report and Written Opinion, European Patent Office, Sep. 20, 2019, 9 pages.
State Intellectual Property Office of People's Republic of China, First Office Action CN No. 201980064761.4, Aug. 9, 2023, China.
State Intellectual Property Office of People's Republic of China, Second Office Action issued in corresponding Application No. 201980064761.4, dated Feb. 21, 2024, 18 pp.
Australian Government, Intellectual Property Australia; Examination Search Report No. 1; Date of Report: Apr. 2, 2024; pp. 1-4.
Canadian Intellectual Property Office; Office Action; Dated: Mar. 7, 2024; pp. 1-3.

* cited by examiner

AIRWAY DEVICE

This application is a U.S. national stage application under 35 U.S.C. § 371 of PCT International Application Serial No. PCT/GB2019/051822 which has an international filing date of Jun. 27, 2019, designates the United States of America, and claims the benefit of GB Application No. 1812562.5, which was filed on Aug. 1, 2018. The disclosures of each of these prior applications are hereby expressly incorporated by reference in their entirety.

This invention relates to an airway device for the ventilation of patients, and in particular, relates to a laryngeal mask airway device.

BACKGROUND

Traditionally, endotracheal tubes have been used to establish an airway in an unconscious patient. Endotracheal tubes comprise an elongate tube having an inflatable cuff, or balloon positioned at the tube's distal end. In use, the distal end of the endotracheal tube is inserted into the patient's trachea via the patient's mouth. Once correctly positioned, the cuff is inflated to form a seal with the interior lining of the trachea, which prevents aspiration of gastric fluid into the patient's lungs. The proximal end of the tube is connected to a ventilation device for providing positive pressure to ventilate the patient's lungs.

However, endotracheal tubes have several disadvantages including being difficult to correctly position within a patient's airway and requiring significant manipulating of a patient's head and neck in order to insert the tube, which in some patients, such as those suffering a neck or spinal injury, may be highly undesirable. Furthermore, since the distal end of the endotracheal tube is positioned within the trachea and necessarily passes through the laryngeal structures, it is not uncommon for a patient to suffer from some degree of laryngeal morbidity such as post-operative hoarseness, or dysphagia.

Laryngeal mask airway devices (hereinafter "laryngeal masks") were therefore developed with the aim of overcoming the aforementioned disadvantages associated with endotracheal tubes. In contrast to the endotracheal tube, laryngeal masks are relatively easy to insert to establish an airway in a patient, and only require relatively minor manipulation of the patient's head and neck in order to correctly position the mask. Importantly, and in contrast to endotracheal tubes, the laryngeal mask provides ventilation of a patient's lungs without contacting the sensitive inner lining of the trachea or laryngeal structures, thus reducing the occurrence of post-operative complications such as those listed above.

In general terms, known laryngeal masks typically comprise an airway tube opening at one end into the interior of a hollow mask portion. The mask portion is shaped to fit over the larynx of a patient. The periphery of the mask is often formed by a cuff which in use forms a seal around the laryngeal opening, thus establishing an effective airway.

However, to ensure that a seal is adequately formed, it has been necessary to provide laryngeal masks in a variety of sizes, so as to suit different sizes of patient. For example, the diameter of the airway tube and the proportions of the mask part, respectively, can be varied so as to be suitable for a particular weight range of a patient, e.g. "small adult (30-50 kg), "medium adult" (50-70 kg) and "large adult" (70+kg), each of whom will have different sizes of laryngeal region.

Selection of the suitable size of laryngeal mask is typically based on a manufacturer's recommendation of weight-based estimate, plus clinical judgement. However, it will be appreciated that the natural and potentially unpredictable variations in patient anatomy mean that these selection parameters may not necessarily suit each patient's needs.

It is also known to provide a drainage tube within a laryngeal mask for draining fluid such as gastric fluid from the patient's oesophagus that enters the mask. The drainage tube may be arranged substantially parallel to the airway tube within a housing of mask. Such a drainage tube is typically a passive venting tube that is open to the atmosphere at the distal end of an elongate neck portion of the mask, which extends from the mask portion, and open at the proximal end within the mask portion to receive any fluid collecting in the mask.

However, such drainage tubes may also collect other fluids, such as fluid from the supraglottic region. It can therefore be difficult to monitor the quantity of each particular fluid being produced, and also may require additional patient monitoring to ensure that fluid does not build up within the mask portion, causing aspiration of the fluid by the patient.

A further disadvantage of known laryngeal masks is that they cause pressure, both during insertion and ventilation on the back of the tongue and epiglottis of a patient. This problem is particularly prevalent in newer laryngeal masks that adopt a wider neck part, and also in patients with a high basal metabolic index (BMI), as the tongue and tissues within the airway, such as the epiglottis and surrounding structures are often enlarged as a result of the increased BMI.

Compression of the tongue and surrounding structures can cause physiological problems and laryngeal morbidity, such as damage to the hypoglottal and lingual nerves, respectively.

Embodiments of the present invention seek to address at least some of the aforementioned problems.

BRIEF SUMMARY OF THE DISCLOSURE

In accordance with an aspect of the present invention there is provided a laryngeal mask comprising a housing, the housing comprising a neck part and a head part extending from a first end of the neck part; the head part comprising a sealing face and an opposing face; the sealing face and the opposing face being connected by an enclosing wall extending upwardly from the sealing face; the sealing face comprising a seal for forming a seal around a larynx and having an opening arranged to be positioned over a laryngeal opening; and wherein the mask further comprises an airway tube positioned within the housing and extending from a second end of the neck part to the opening in the seal; wherein the head part comprises a resiliently deformable portion positioned between the sealing face and the opposing face, the resiliently deformable portion being a preferentially deformable portion of the head part.

The preferentially deformable portion of the head part is a portion specifically configured and arranged to be compressible as compared to the remainder of the head part which may, or may not, be at least partially deformable or compressible by virtue of the materials and/or configuration from which the head part is formed. Therefore, embodiments of the present invention provide a specific means of enabling the dimensions of at least a specific portion of the head part to be adjustable by compression and expansion of the preferentially deformable portion that cannot be achieved by the prior art which lacks this preferentially deformable feature.

The resiliently deformable portion enables the mask to be fitted to a wider range of patients as compared to prior art devices, as the resiliently deformable portion compresses to allow ease of insertion of the device, and then expands towards its uncompressed state so as to fill the available space in the patient's laryngeal region. In this way, a custom anatomical fit is achieved as the resiliently deformable portion expands in a controlled manner, without having to select a particular size of mask depending on a patient's specific weight.

It will therefore be appreciated that the arrangement of embodiments of the present invention have at least the advantage of eliminating the potential for incorrect selection based primarily on manufacturer's weight recommendations, as the head of the mask is able to resiliently deform to achieve a clinically satisfactory seal when used across a significantly extended weight range of patients, as compared to the prior art arrangements, as will be explained.

The resiliently deformable portion may comprise a protrusion or a projection.

The protrusion or projection comprising the resiliently deformable portion may protrude or project upwardly from the opposing face of the housing.

The protrusion or projection is preferably shaped so as to conform anatomically with respect to the laryngeal region of the patient. Such a shape may include, but not be limited to a dome-shape. This configuration may contribute to the mask's ability to fit a wide weight range of patient as compared to prior art arrangements, because the protrusion or projection can expand to fill the available space in the laryngeal region, almost irrespective of the patient's weight or size.

The resiliently deformable portion may be movable between a first, compressed position in which the head part is generally flattened and a second, uncompressed position in which the head part is generally extended.

The resiliently deformable portion may comprise a compressible material.

The head part may further comprise a cavity.

The cavity may comprise a fluid sump for the collection of fluid from the supraglottic or other regions of a patient.

The cavity may comprise or be in fluid connection with one or more drain tubes or apertures connectable to one or more drain tubes or suction tubes for draining fluid from the cavity or sump.

The inner peripheral edge of the cavity may be bevelled. The bevelled edge may assist in reducing tissue trauma caused during insertion of the mask into the airway of a patient and/or may prevent excessive compression or control the extent of compression of the resiliently deformable portion by providing a surface against which at least a part of the resiliently deformable portion can abut during compression.

The cavity may be hollow or filled, or partially filled with a resiliently deformable material or fluid. In one or more embodiments, the cavity may comprise a resiliently compressible structure, such as a concertina-like structure.

The resiliently deformable portion may overlie at least a part of the cavity. The cavity may provide a space into which a part of the head portion, for example the opposing face, can be temporarily received into, so as to temporarily reduce the volume of the head part. This temporary reduction in volume and/or size of the head part improves ease of insertion of the device.

The head part may comprise one or more apertures.

The head part may comprise two apertures.

The one or more apertures may be generally eye-shaped, or generally semi-circular, or generally tear-drop shaped. These example configurations cause the apertures to resist closure and to biased towards an open configuration. It will therefore be understood that the shape of the one or more apertures may be of any shape suitable for biasing the aperture(s) towards an open configuration. The aforementioned aperture shapes respectively assist with returning the resiliently deformable portion of the head part towards an uncompressed configuration after it has been compressed.

The one or more apertures may be positioned adjacent the resiliently deformable portion.

The one or more apertures may extend substantially around two-thirds the length of the head part.

The apertures may be positioned opposite to one another in the enclosing wall of the head part.

The one or more apertures may be in fluid communication with the cavity.

The apertures may be arranged to abut one or more surfaces of a patient's airway.

The head part may comprise a tapered portion, such as a tapered distal portion. The taper may be in more than one plane of the device. By way of non-limiting example, the distal portion may be tapered in the horizontal and vertical planes, such that the opposing face and the enclosing wall of the head part converge towards a tip. For example, the head part may be generally tear-drop shaped.

The tapered portion may improve ease of insertion of the mask into a patient's airway by enabling a clinician to present the narrow distal portion of the mask first into the patient's airway so as to guide the mask into the correct position within the airway. This ease of insertion is further enhanced by the capability of the head part to further reduce in size in the region of the resiliently deformable portion, as will be explained.

The head part may further comprise an epiglottic rest, for contacting the patient's epiglottis when the mask is in use. The epiglottic rest may be positioned on a proximal end of the sealing face.

The head part between the top of the resiliently deformable portion and the sealing face 18 may compress or reduce in height by an amount X, as compared with an uncompressed height of the head part of Z.

Amount X may be, for example, around 12 mm to 17 mm, for example around 13.5 mm to 16.5 mm, for example 15 mm.

In the uncompressed configuration, amount Z may be, for example, around 36 mm to 44 mm, for example, around 36 mm to 44 mm, for example, 38 mm to 42 mm, for example 40 mm.

In the compressed configuration, amount Z may be, for example, around 20 mm to 29 mm, for example, around 22.5 mm to 27.5 mm, for example, 25 mm.

The ability of the resiliently deformable portion to compress and expand as described herein enables this embodiment of the present invention to be used across a wide range of patients of varying weight, without being restricted to a discreet weight range, as the prior art arrangements are.

For example, an embodiment of laryngeal mask in accordance with the present invention may be provided in adult and paediatric sizes, with the adult size being suitable for at least the majority of adult patients irrespective of their weight.

This is a significant advantage over the prior art, for several reasons. Firstly, it eliminates the requirement for a clinician to select a suitable size of mask depending on patient weight.

Secondly, it virtually eliminates the need for further clinical assessment beyond initial selection of a mask size depending on patient weight.

Thirdly, it avoids a hospital or other clinical environment having to purchase numerous masks of varying sizes, which would ordinarily be required to ensure adequate stock for surgical procedures and patient ventilation. Instead, it is only necessary to purchase, for example, paediatric and adult sizes, each of which can be used interchangeably when ventilating children and adults, respectively, of different weights.

The mask may comprise silicone.

The neck part of the housing may comprise an elongate tube.

The airway tube may extend the length of the neck part and may comprise or be connectable to a connector for a ventilation device or breathing circuit.

The laryngeal mask may comprise one or more of the following features, either in addition to the aforementioned features of the invention, or in one or more alternative embodiments of the aforementioned invention.

For example, according to an aspect of the invention, the laryngeal mask may comprise a housing; the housing comprising a neck part and a head part extending from the a first part of the neck part, the head part comprising a sealing face and an opposing face; the sealing face and the opposing face being connected by an enclosing wall extending upwardly from the sealing face; the sealing face comprising a peripheral seal for forming a seal around a larynx and having an opening arranged to be positioned over a laryngeal opening; and wherein the mask further comprises an airway tube positioned within the housing and extending from a second part of the neck part to the opening in the peripheral seal; wherein the mask further comprises a first drain tube extending from the neck part to an aperture located in a distal tip of the head part, and a second drain tube extending from the neck part to a position within the head part that is proximal to the distal tip.

The distinct first and second drain tubes enable selective draining of particular fluid types from one or more regions of a patient's airway or oesophageal region. This provides at least the additional advantage of enabling a clinician to monitor and optionally measure specific fluid production from a patient.

The drain tubes may be suitable for draining fluid such as, but not limited to gastric fluid and/or fluid from the supraglottic region. The drain tubes may optionally comprise, or be connectable to, a connector for attaching to a suction device, for removing fluid from the drain.

The first drain tube may be for draining gastric fluid.

The second drain tube may be for draining fluid from a supraglottic region of a patient.

The first and second drain tubes may be positioned to one side of, or either side of the airway tube, within the housing.

In use, the aperture in the distal tip of the head part may be positioned adjacent the gastric inlet of a patient.

The housing, and/or airway tube and/or optional drain tubes may comprise a flexible plastic material, or silicone, including but not limited to medical grade silicone. The housing may comprise a gas-impermeable material. The housing and/or airway tube and/or optional drain tubes may, in one or more embodiments, comprise any known suitable material. Preferably, the housing and/or airway tube and/or optional drain tubes are formed from an optically transparent material. Such transparency yields advantages such as easier identification of any obstruction within the housing or tubes.

The housing and/or airway tube and/or optional drain tubes may further comprise a rigid portion or coating or "bite block", which is capable of resisting deformation, such as a result of pressure applied by the patient's teeth or jaw during ventilation. The rigid portion or overcoating or "bite block" therefore serves to maintain the patency of the airway and, optionally, any further tubes such as drain tubes located within the housing. Optionally, the rigid portion, or coating or "bite block" may be a part of a connector for attaching to a ventilation device.

In accordance with another aspect of the present invention there is provided a laryngeal mask, comprising a housing; the housing comprising a neck part and a head part extending from a first end of the neck part, the head part comprising a sealing face and an opposing face; the sealing face and the opposing face being connected by an enclosing wall extending upwardly from the sealing face; the sealing face comprising a peripheral seal for forming a seal around a larynx and having an opening arranged to be positioned over a laryngeal opening; and wherein the mask further comprises an airway tube positioned within the housing and extending from a second end of the neck part to the opening in the peripheral seal; and wherein the neck part comprises a curved portion, the curved portion being adapted to accommodate a proximal portion of a patient's tongue when the mask is in use.

By being adapted to accommodate a proximal portion of a patient's tongue, embodiments of the present invention may avoid compression of the tongue, as thus reduces the likelihood of post-operative complications such as laryngeal morbidity, as compared to prior art arrangements which are not able to accommodate said portion of the tongue. Therefore, the post-operative complications relating to laryngeal morbidity, such as lingual and/or hypoglottal nerve damage, dysphagia and/or hoarseness, may be significantly reduced or eliminated by use of certain embodiments of the present invention.

The curved portion may be adapted to accommodate a portion, for example, a proximal portion of a patient's tongue when the mask is in use. By "proximal portion", it is meant the part of the tongue positioned closest to the laryngeal region of the patient.

By being adapted to accommodate a proximal portion of a patient's tongue, the embodiment of the present invention may avoid compression of the tongue, as this reduces the likelihood of post-operative complications such as laryngeal morbidity, as compared to prior art arrangements which are not able to accommodate said portion of the tongue. Therefore, the post-operative complications relating to laryngeal morbidity, such as lingual and/or hypoglottal nerve damage, dysphagia and/or hoarseness, may be significantly reduced or eliminated by use of certain embodiments of the present invention.

In one or more embodiments of the present invention, the curved portion may comprise a first section, the first section may extend from a proximal portion of the head part.

The curved portion may further comprise a second section. The second section may extend from a proximal portion of the neck part.

The curved portion may further comprise a third section. The third section may extend between the first and second sections.

The first and third sections may be continuous with one another.

The second and third sections may be continuous with one another.

The first, second and third sections may be continuous with one another.

The first section may extend away from the direction of the head part at an angle substantially between 40 to 50 degrees relative to an axis that is generally perpendicular to the plane of the sealing face.

The first section may extend away from the direction of the head part at an angle of substantially 45 degrees relative to the axis.

The second section may extend away from the direction of the third section and towards the direction of the second end of the neck part at an angle substantially between 90 and 100 degrees relative to an axis that is generally perpendicular to the plane of the sealing face.

The second section may extend away from the direction of the head part at an angle of substantially 95 degrees relative to the axis.

The third section may extend away from the direction of the head part and towards the direction of the second section, at an angle substantially between 78 and 83 degrees relative to an axis that is generally perpendicular to the plane of the sealing face.

The third section may extend away from the direction of the head part and towards the direction of the second section at an angle of substantially 81 degrees relative to the axis.

The first section may extend away from the direction of the head part at an angle of substantially 45 degrees relative to the axis, and the third section extends away from the first section at an angle of substantially 36 degrees relative to an edge of the first section.

The second section may extend away from the third section towards the direction of the second end of the neck part, at an angle of substantially 14 degrees relative to an edge of the third section.

The curved portion may comprise an angle of between around 90 to 100 degrees between an axis which lies generally perpendicular to the plane of the sealing face, and the second end of the neck part. The angle may be around 95 degrees.

BRIEF DESCRIPTION OF THE DRAWINGS

Embodiments of the invention are further described hereinafter, by way of example, and with reference to the accompanying drawings, in which.

DETAILED DESCRIPTION

Referring to the drawings, an embodiment of laryngeal mask 10 comprises a housing 12, the housing 12 having an elongate neck part 14 and a generally tear-drop shaped head part 16 extending from a first end of the neck part 14.

The mask 10 comprises medical grade silicone, which is known to provide a suitable amount of flexibility and rigidity respectively as required in laryngeal masks and other similar airway devices.

The head part 16 comprises a sealing face 18 and an opposing face 20. As best seen on FIG. 5, the sealing face 18 and opposing face 20 are connected by an enclosing wall 22 which extends upwardly from the sealing face 18 to meet the opposing face 20.

Figure 1:
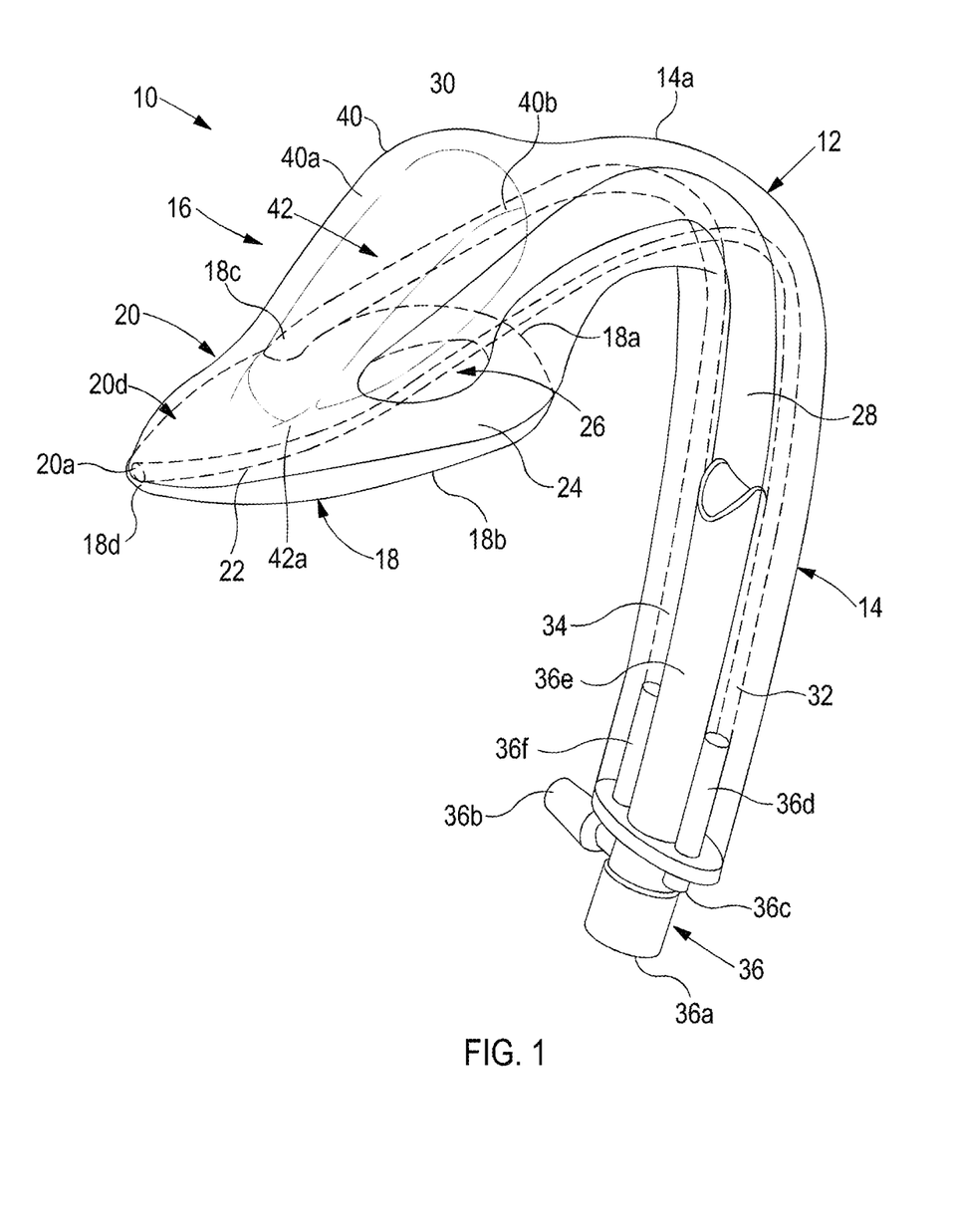
FIG. 1 is a perspective view of an embodiment of a laryngeal mask according to the invention.

As best seen in FIG. 1, the sealing face 18 comprises a seal 24 for forming a seal around the larynx of a patient and has a generally circular opening 26 which is arranged to be positioned over the patient's laryngeal opening. The sealing face 18 is generally tear drop shaped, having a curved proximal end wall 18a and two converging side walls 18b, 18c which converge towards a generally pointed distal region, or distal tip 18d. The generally circular opening 26 is positioned along the midline of the sealing face 18 and towards the curved proximal end wall 18a.

The mask 10 further comprises an airway tube 28 which extends from one end of the neck portion 14 to the opening 26 in the seal 24, for ventilating the patient.

The head part 16 further comprises a resiliently deformable portion 30 on the opposing face 20, which is compressible to controllably alter the size of the head part 16, as will be explained.

Figure 2:
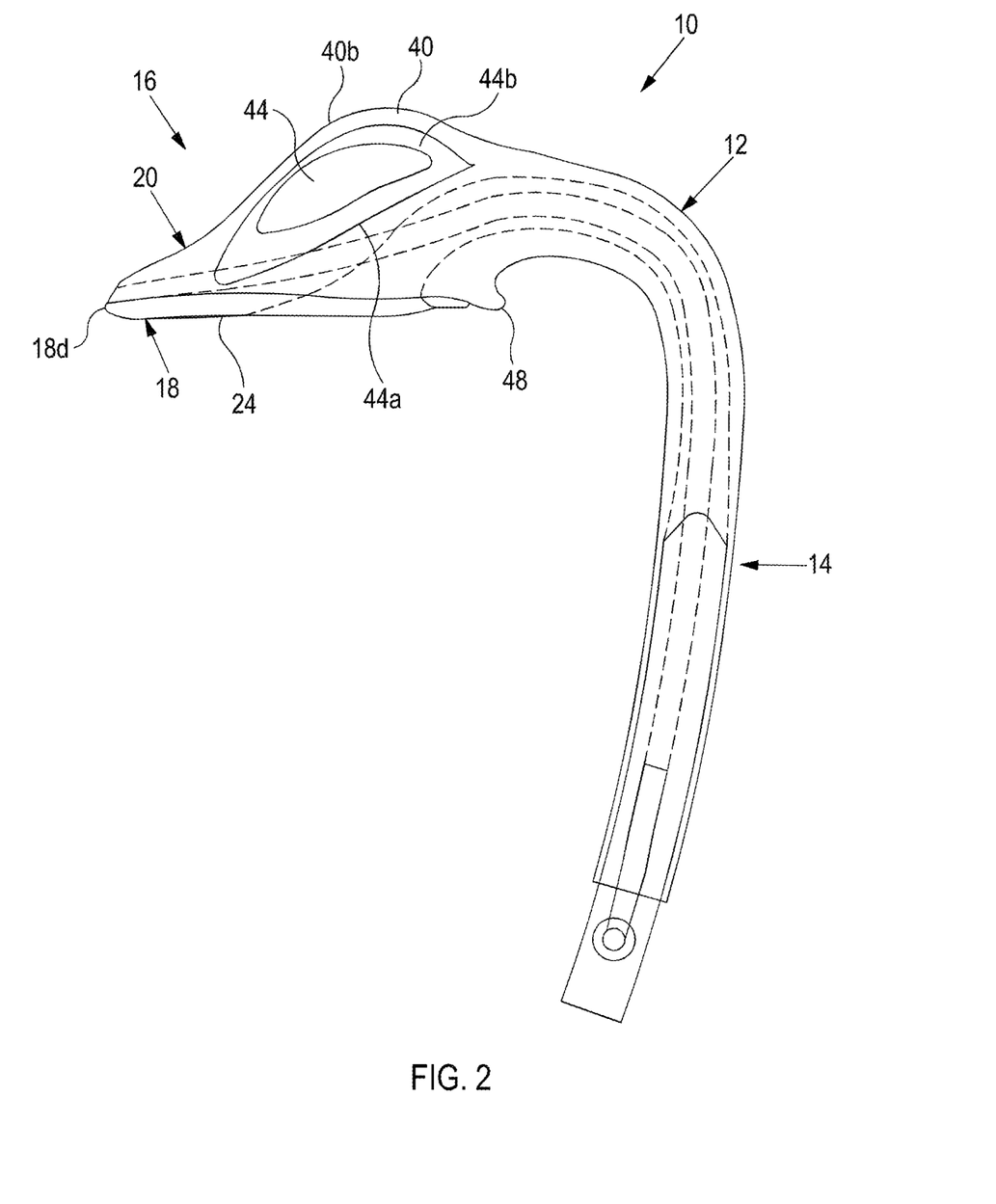
FIG. 2 is a left side view of the embodiment shown in FIG. 1.
Figure 3:
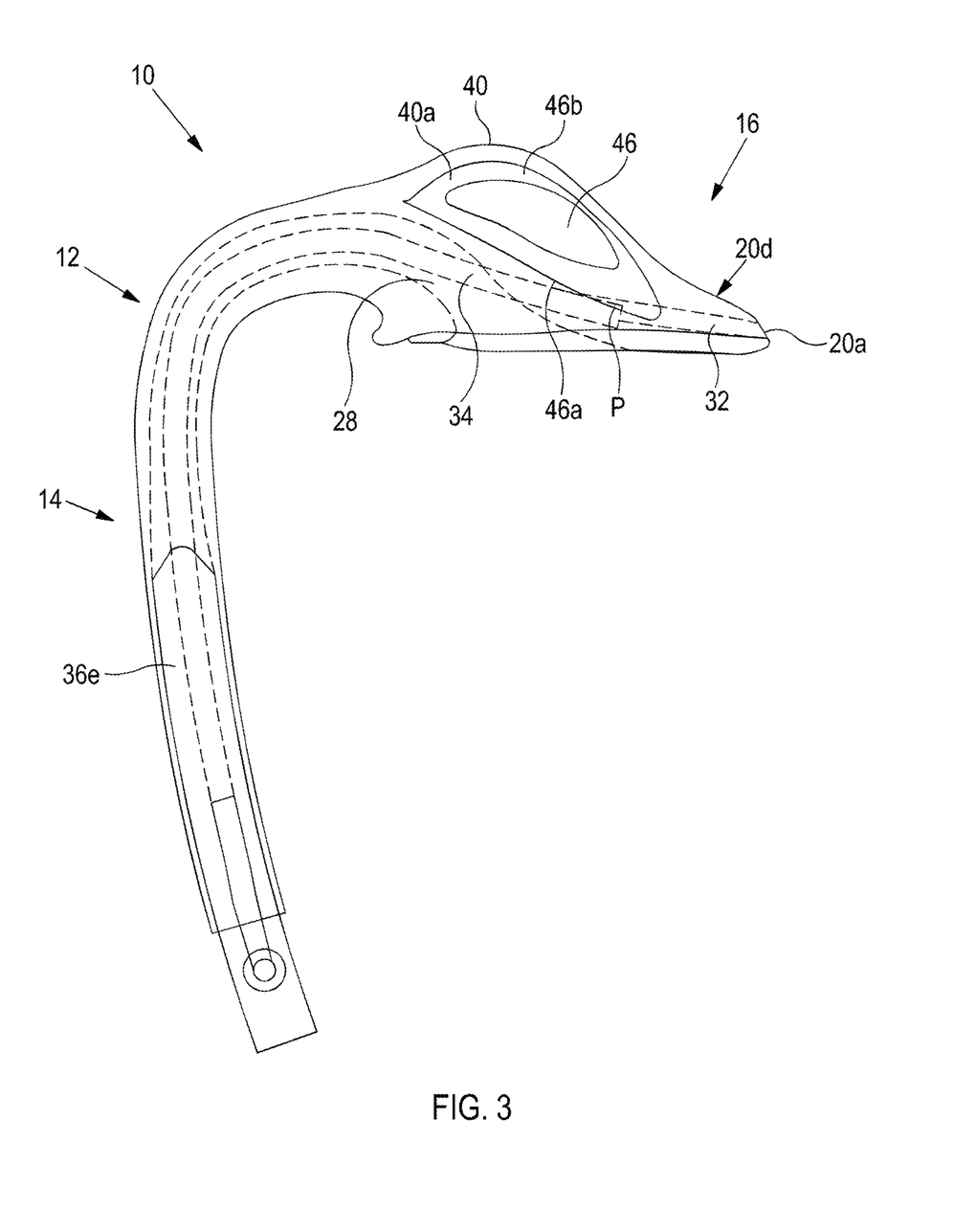
FIG. 3 is a right side view of the embodiment shown in FIG. 1.

Referring in particular to FIGS. 1 to 3, the mask 10 comprises the airway tube 28 disposed centrally within the housing 12 and extending from a distal end (i.e. in, use, the end that is furthest away from the patient, namely that extending from the patient's mouth) of the neck part 14 into the head part 16 and terminating at the opening 26 in the seal 24. For the avoidance of doubt, it is clarified that the proximal end of the neck part 14 is the end adjoining a proximal portion of the head part 16. The distal portion, or distal tip of the head part 16 is defined as the portion furthest away from the neck part 14 of the mask.

The present embodiment of mask 10 further comprises a first and second drain tube 32, 34. The first drain tube 32 comprises a gastric fluid drain tube 32 and the second drain tube comprises a supraglottic fluid drain tube 34. The first and second drain tubes 32, 34 are located either side of the airway tube 28 and extend between the distal end of the neck part 14 and into the head part 16.

Figure 5:
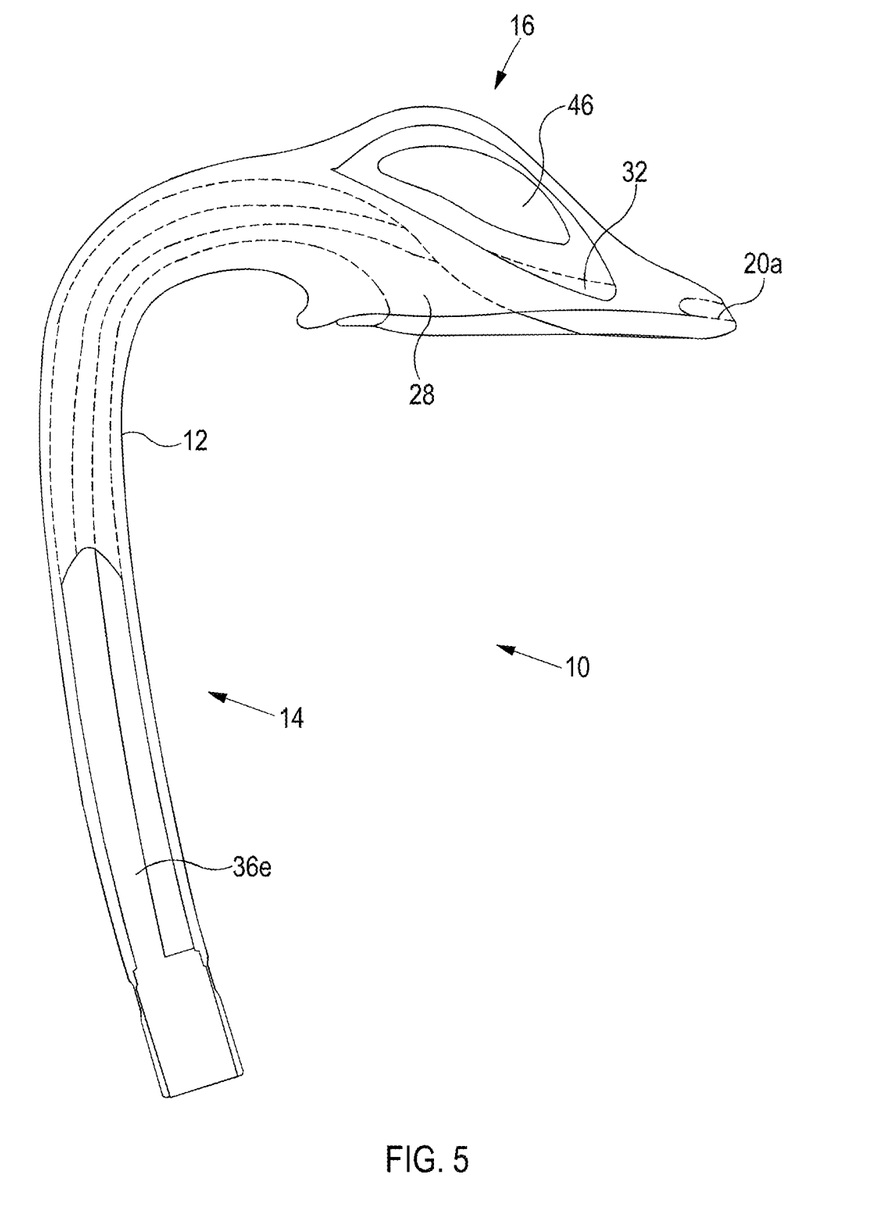
FIG. 5 is a right side sectional view of the embodiment shown in FIG. 1, showing the relative positioning of the components of the mask.
Figure 6:
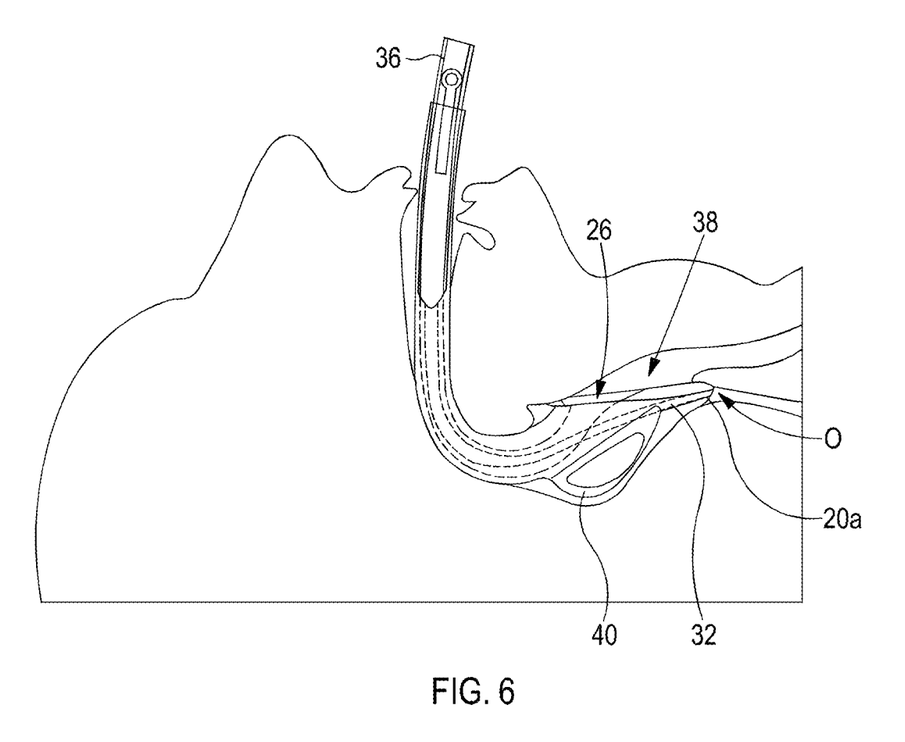
FIG. 6 is a cross sectional view of the embodiment of mask of FIG. 1 positioned within a patient's airway.

Specifically, and as best seen from FIGS. 5 and 6, the first, gastric drain tube 32 extends from the distal end of the neck portion 14 and into the head portion 16 terminating at a distal aperture 20a positioned centrally in the distal tip of a nose portion 20d of the opposing face 20.

The housing 12, airway tube 28 and drain tubes 32, 34 each comprise medical grade silicone, which maintains sufficient structure to ensure patency of the mask 10 and component tubes 28, 32, 34 in use, whilst enabling some flexibility to facilitate insertion of the mask 10 into a patient's airway.

The distal end of the neck part 14 housing 12 comprises a connector 36 for connecting the distal end of the airway tube 28 to a breathing circuit (not shown) to enable positive pressure to be applied to the lungs of a patient via a ventilation device (not shown).

In the present embodiment, the connector 36 comprises a first female seating part 36a for connecting to the corresponding male part of a breathing circuit (not shown), a second female seating part 36b for connecting to a suction device (not shown), an open gastric vent 36c and three upwardly extending hollow tubes 36d, 36e, 36f, each extending into the distal portion of each of the gastric fluid drain tube 32, airway tube 28 and supraglottic fluid drain tube 34, respectively.

The connector 36, including the three upwardly extending hollow tubes 36d, 36e, 36f, comprises relatively incompressible and inflexible plastic in order to function as a "bite block", i.e. to maintain patency of each of the airway tube 28 and drain tubes 32, 34 by resisting compression, in the event that a patient's jaw presses against the flexible silicone material of the housing 12 and aforementioned airway tube 28 and drain tubes 32, 34.

The airway tube "bite block" 36e extends substantially half way along the portion of the airway tube 28 positioned in the neck portion 14, so as to extend, in use, both proximally and distally with respect to the patient's jaw to protect the distal part of the airway tube 28 that lies, in use, within and extending from, the patient's mouth.

The proximal end of the airway tube 28 terminates at the opening 26 in the seal 24 that forms the sealing face 18 of the head part 16. As best illustrated in FIG. 6, in use and once correctly positioned, the opening 26 lies adjacent the laryngeal inlet 38 of the patient.

The opposing face 20 of the head part 16 comprises a protrusion 40 the lateral edges of which are defined by two ribs 40a, 40b, which emerge from a top face 14a of the proximal region of the neck part 14. The protrusion 40 is arranged so as to substantially overlie the opening 26 in the seal and extends away from the sealing face 18 so as to define a void or cavity 42 between the sealing face 18 and the opposing face 20 in the proximal region (i.e. that closest to the neck part 14) of the head part 16. The opposing face 20 of the head part 16 tapers downwardly and inwardly from the distal side of the protrusion 40 towards the distal tip 18d of the sealing face 18d. The two ribs 40a, 40b defining the lateral edges of the protrusion 40 taper downwardly so as to merge into the opposing face 20 to form a nose portion 20d. Consequently, the enclosing wall 22 converges from a point substantially aligned with the opening 26 in the seal 24, towards the distal tip 18d of the sealing face 18, which, in combination with the tapered nose portion 20d of the opposing face 20, forms a generally tear-drop shaped head part 16.

The inner edge of the void or cavity 42 comprises a bevelled peripheral edge 42a against which the resiliently deformable portion 30 can abut. The bevelled peripheral edge 42a also acts to retain any fluid from the supraglottic region, that may collect in the cavity 42 so that it can be suctioned out via the supraglottic drain tube 34. The bevelled peripheral edge 42a portion also serves to streamline the head part 16 which may reduce the likelihood of tissue damage during insertion of the mask 10.

In the present embodiment, enclosing wall 22 of the head part 16 comprises two opposing apertures 44, 46, each aperture 44/46 being positioned below the protrusion 40 and in communication with the cavity 42. The apertures 44, 46 are generally eye-shaped, having a substantially planar base wall 44a and a curved top wall 44b, each of which is at least partially bevelled to reduce the likelihood of tissue trauma during insertion of the mask. The proximal and distal ends of the top wall 44b extend downwardly to meet the base wall 44a. The curved top wall 44b configuration causes the aperture 44 to maintain the eye-shape arrangement unless pressure is applied to the projection 40 to cause it to compress, such as when the head part 16 is being passed through the relatively narrow pharyngeal region during insertion of the mask 10 into a patient's airway.

Figure 4:
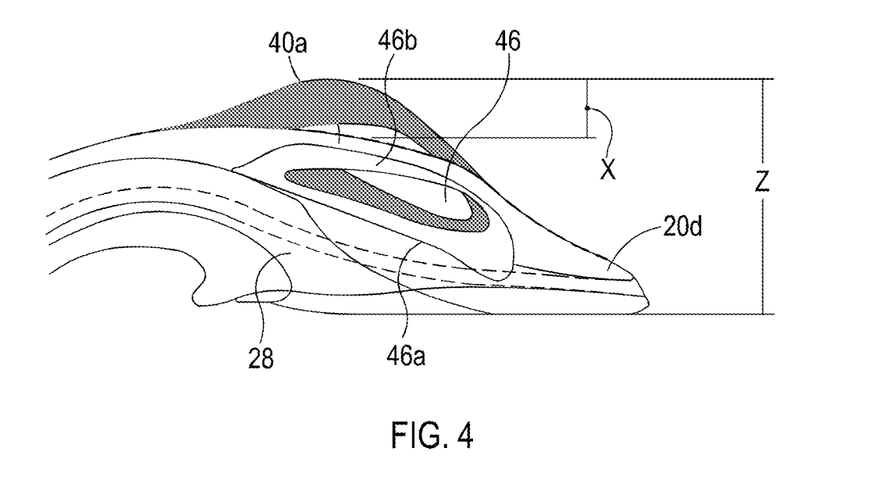
FIG. 4 is a view of the head part of the embodiment shown in FIG. 1, showing deformation of the resiliently deformable portion of the head part.

As best seen in FIG. 4, the aperture 46 is temporarily flattened or closed during the aforementioned compression, thus reducing the height of the head part 16 by an amount X. In the present embodiment, the amount X is 15 mm. The uncompressed configuration of the aperture 44 and resiliently deformable portion 30 is represented by the grey shading in FIG. 4.

Conversely, when the mask 10 is in the correct position within the patient's airway such that the head part 16 is positioned within the laryngeal region of a patient, the closed or partially closed aperture 46 gradually reopens to fill the available space in the laryngeal region by virtue of the aforementioned configuration of the aperture, namely the circular top wall 46b regaining its original shape due to the resilient nature of the silicone from which the mask 10 is formed. In the present embodiment, the height Z of the uncompressed head part 16 between the top of the resiliently deformable protrusion 30 and the sealing face 18 is 40 mm.

As will be appreciated with particular reference to FIG. 4, as the resiliently deformable portion 30 gradually regains its original uncompressed configuration once the head part 16 is in position within the laryngeal region of the patient, the resiliently deformable portion 30 expands until it contacts the inner surface of the patient's airway, thus forming an anatomically shaped fit that is customised to the size and shape of the patient's laryngeal region and airway. In this way, the present laryngeal mask can be used on a wide variety of patients of significantly varying weights, in contrast to prior art arrangements that must be provided in a number of different sizes in order to accommodate different weight ranges of patients.

Figure 7:
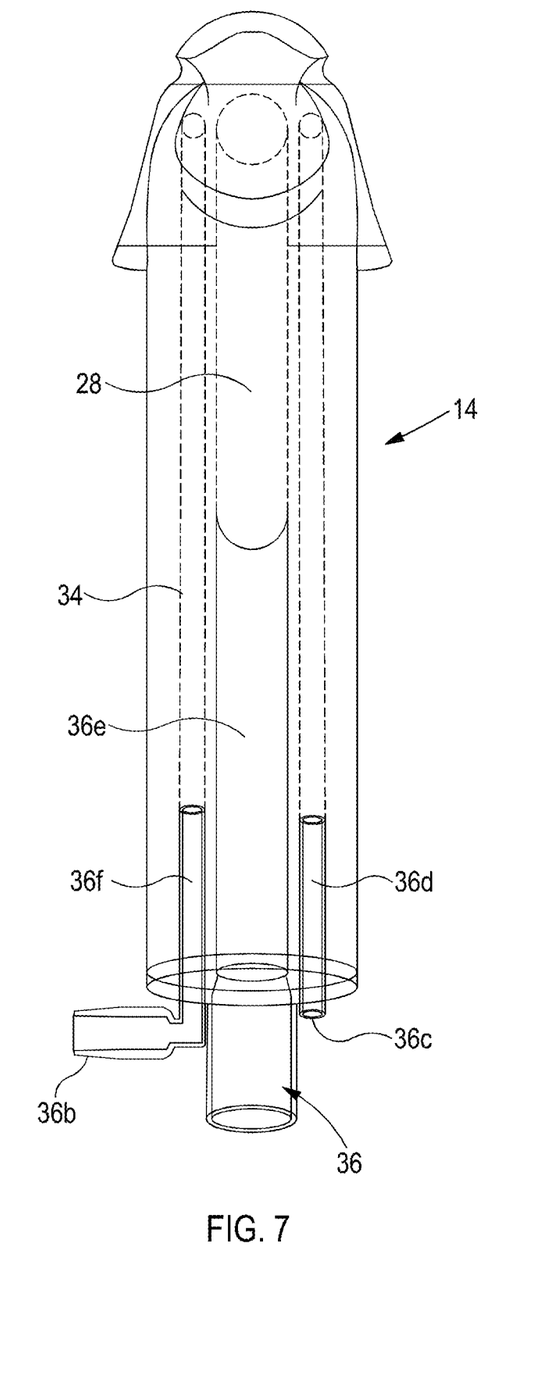
FIG. 7 is a front view of the embodiment of mask of FIG. 1, showing the relative configuration of the airway tube and drain tubes.
Figure 8:
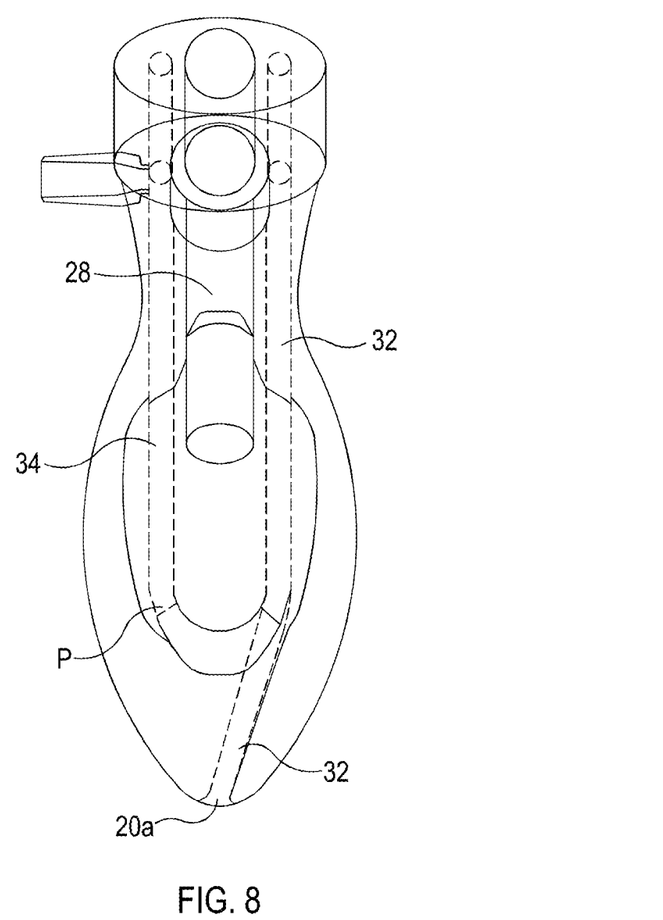
FIG. 8 is a plan view of the embodiment of mask of FIG. 1, showing the relative configuration of the airway tube and drain tubes.

In use, and as best seen in FIG. 7, as the distal aperture 20a is positioned at the most distal point of the head part 16, it can abut or be placed adjacent to the gastric (oesophageal) inlet O of a patient. This positioning means that any gastric fluid refluxing from the stomach is immediately captured by the adjacent distal aperture 20a and flows into the gastric drain 32, thus significantly minimising the risk of aspiration of the fluid by the patient.

The second, supraglottic fluid drain tube 32 extends from the distal end of the neck portion 14 and into the cavity of the head part 16 so as to terminate proximal to the distal aperture 20a of the head part 16. In the particular described embodiment, the terminus P of the second fluid drain tube 34 is positioned approximately two thirds of the way along the head part 16, and approximately one third of the way across the head part 16 when viewed in plan view. This terminus P is approximately midway between the generally circular aperture 26 in the seal 18 and the distal aperture 20a.

In use, any supraglottic fluid produced by the patient enters the cavity 42 via the apertures 44, 46 in the head part 16, where it collects to such a level where it meets the terminus P of the second, supraglottic fluid drain tube 34. The supraglottic fluid can then be actively or passively drained from the cavity 42, via drain tube 34 and a connector 36 and optional suctioning equipment, as will be explained. In particular, by connecting suctioning equipment to the second female seating part 36b which is in fluid connection with the supraglottic fluid drain tube 34, supraglottic fluid can be suctioned from the cavity 42 and through the drain tube 34, thus significantly minimising the risk of aspiration of the fluid by the patient.

The distinct first and second drain tubes, with their corresponding distinct termini P, 20a, mean that supraglottic fluid can be collected and drained separately to gastric fluid, which provides the advantages previously explained.

The housing 12, airway tube 28 and drain tubes 32, 34 each comprise medical grade silicone, which maintains sufficient structure to ensure patency of the mask 10 and component tubes 28, 32, 34 in use, whilst enabling some flexibility to facilitate insertion of the mask 10 into a patient's airway.

The present embodiment of mask further comprises an epiglottic rest 48, upon which a patient's epiglottis can rest during use of the device. This creates more space in the curved region of the neck part for accommodating the proximal portion of the patient's tongue, as the epiglottis is held away from the space occupied by the tongue.

Figure 9:
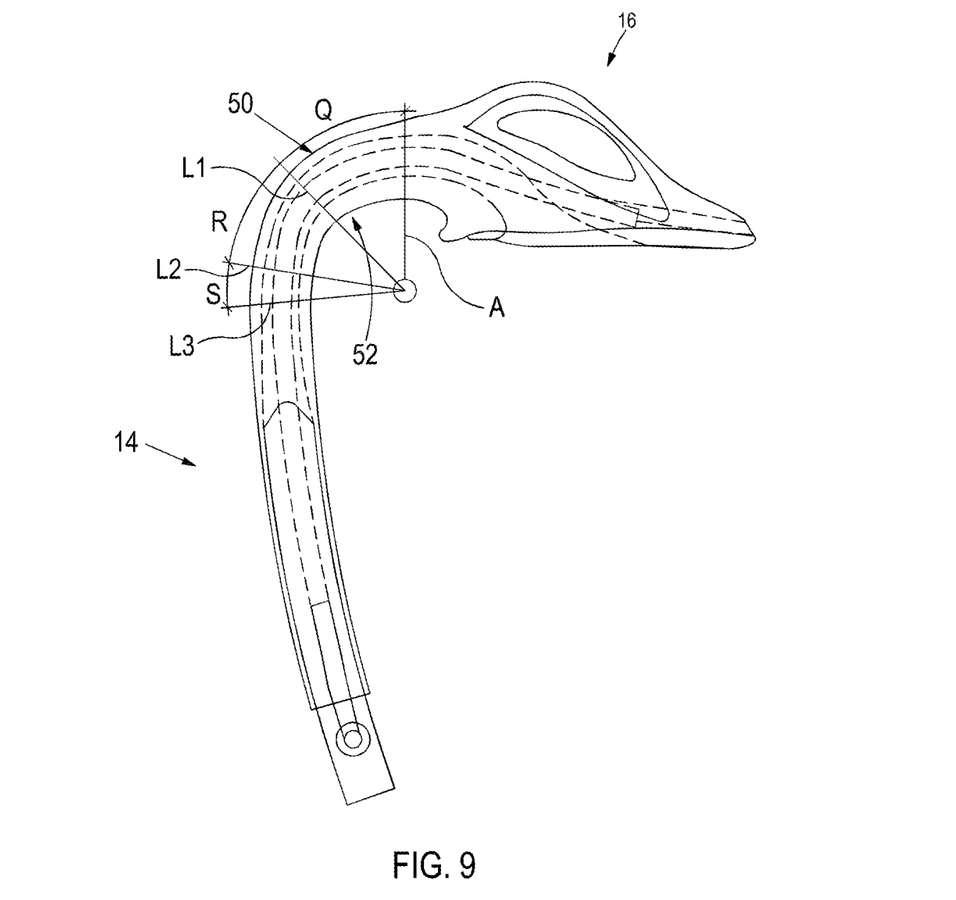
FIG. 9 is a right side view of the embodiment shown in FIG. 1, showing a portion of the neck part in theoretical sections, for the purposes of explaining the arrangement of the mask in further detail.

As best seen from FIGS. 6 and 9, and as mentioned above, the neck part of the housing comprises a curved portion which is adapted to accommodate a proximal portion of a patient's tongue, when the mask is in position within a patient's airway.

The shape and configuration of the curve of the present invention creates room for a patient's tongue when it is in a natural resting position whilst the patient is unconscious. With the aim of explaining this shape and configuration further, the curved portion will be described with reference to sections of the curve. However, it is to be appreciated that the term "section" or "sections" is not intended to be limiting, nor is intended to suggest that the neck portion is, or must be, formed in a sectional arrangement. The terminology is merely intended to clarify the relative configuration of the curve.

Similarly, with the aim of defining the curved portion in more detail, the use of the terms "first side" and "second side" are used to describe areas of the curved portion by way of non-limiting terminology. The "first side" 50 of the curved portion can be considered as the side extending from the opposing face 20 of the head part 16 and the "second side" 52 can be considered as the side extending from the sealing face 18 of the head part 16, via the epiglottic rest 48.

The curved portion sits between the head part 16 and the neck part 14 and extends from the proximal portion of the head part 16, curving downwardly away from the direction of the head part 16 to continuously meet the elongate neck part 14.

In the present embodiment, the approximate angle Q+R+S between the proximal part of the neck portion 14 which meets the curved portion, i.e. in the region of theoretical line L3, and an axis A which lies substantially perpendicular to the sealing face 18 of the head part 16, is 95 degrees, thus forming a generally L-shaped configuration.

In use, the proximal part of a patient's tongue rests against the second side 52 of the curved portion, while the first side 50 lies generally abuts the pharyngeal and laryngeal regions of the patient.

The curved portion comprises a first section Q, a second section S, and a third section R. The first section Q extends from the proximal part of the head part 16, the second section S extends upwardly from the neck part 14, and the third section R fluidly connects the first and second sections 54, 56.

The airway tube 28, and first and second drain tubes 32, 34 also conform to the same curvature and so their respective curves are the same as that described for the neck part 14 of the housing 12.

Referring in particular to FIG. 9, the second side 52 of the first section Q extends in a plane that is substantially parallel with respect to the sealing side 18. The first side 50 of the first section Q generally follows this plane, but slopes slightly upward towards the head part 16, so as to merge into the projection 40 positioned on the opposing face 20.

Referring to the axis A that lies substantially perpendicular with respect to the sealing surface 18, the first section Q extends away from the head part 16 at an angle of around 45 degrees, such that when the mask 10 is viewed from a right side elevation, with the head part 16 uppermost and neck part 14 extending downwardly, such as illustrated in FIG. 3, the first section Q can be seen to define a proximal part of the curved portion and a part which accommodates at least the majority of the proximal part of a patient's tongue, when the mask 10 is in use. A theoretical line L1 drawn between the first and second sides 50, 52 of the first section Q at the aforementioned 45 degree point may be considered a theoretical edge, for the purpose of defining the curved portion in more detail. The term "theoretical edge" is not intended to reflect a physical edge or boundary with the curved portion.

The third section R of the curved portion extends at an angle of around 36 degrees, relative to the theoretical edge L1 of the first section Q, such that, when the mask 10 is viewed from the aforementioned right side elevation, the third section R curves downwardly towards the second, distal end of the neck part 14. A theoretical line L2 drawn between the first and second sides 50, 52 of the third section R at the aforementioned 36 degree point may be considered a theoretical edge, for the purpose of defining the curved portion in more detail. The term "theoretical edge" is not intended to reflect a physical edge or boundary with the curved portion.

The second section S of the curved portion extends at an angle of around 14 degrees, relative to the theoretical edge L2 of the third section R, such that, when the mask 10 is viewed from the aforementioned right side elevation, the second section S curves downwardly towards the second, distal end of the neck part 14. A theoretical line L3 drawn between the first and second sides 50, 52 of the second section S at the aforementioned 14 degree point may be considered a theoretical edge, for the purpose of defining the curved portion in more detail. The term "theoretical edge" is not intended to reflect a physical edge or boundary with the curved portion.

Accordingly, and as can be appreciated from the Figures, the curved portion of the neck part 14 arranges the neck part 14 at substantially 95 degrees relative to an axis A which is generally perpendicular to the sealing face 18.

As explained above, this particular configuration of curved portion provides sufficient room to accommodate a proximal portion of a patient's tongue, without causing compression of the tongue, thus significantly reducing the likelihood of post-operative complications arising from use of laryngeal masks.

The invention is not intended to be limited to the details of the foregoing embodiments, which are described by way of example only.

For example, it may be noted from FIG. 9 that a dimension of 14 mm is indicated in the neck part. However, this is not intended to be a limiting notation and instead is simply an indication of a suitable dimension for an embodiment of the present invention.

Similarly, some of the relative dimensions and angles are suggested by way of lines surrounding the embodiment of mask shown in FIG. 9. However, these are not intended to limit the invention to any particular configuration or dimensions, relative or otherwise, unless indicated herein.

By way of further example, the optional features of one or more aspects of the invention described herein are not limited to any particular embodiment of the invention. Therefore, it is to be understood that any combination of features described herein can be combined to define a laryngeal mask according to the invention.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. A laryngeal mask, comprising a housing;
   the housing comprising a neck part and a head part extending from a first end of the neck part, the head part comprising a sealing face and an opposing face;
   the sealing face and the opposing face being connected by an enclosing wall extending upwardly from the sealing face, the opposing face comprising a protrusion; the sealing face comprising
   a peripheral seal for forming a seal around a larynx and having an opening arranged to be positioned over a laryngeal opening; and
   wherein the mask further comprises an airway tube positioned within the housing and extending from a second end of the neck part to the opening in the peripheral seal; and
   wherein the head part comprises a resiliently deformable portion comprising the protrusion, the protrusion being arranged to overlie the opening in the sealing face and extend away from the sealing face so as to define a cavity between the sealing face and the opposing face;
   wherein the resiliently deformable portion is moveable between an uncompressed position and a compressed position during compression of the head part between the opposing face and the sealing face; and
   wherein the cavity comprises a fluid sump for receiving fluid from a supraglottic or other region of a patient and is configured to receive at least a part of the opposing face comprising the protrusion during compression of the head part between the opposing face and the sealing face.

2. A laryngeal mask as claimed in in claim 1, wherein the resiliently deformable portion comprises a compressible material.

3. A laryngeal mask as claimed in claim 1, wherein an inner peripheral edge of the cavity is bevelled.

4. A laryngeal mask as claimed in claim 1, wherein the cavity is hollow.

5. A laryngeal mask as claimed in claim 1, wherein the resiliently deformable portion is arranged to overlie at least a part of the cavity.

6. A laryngeal mask as claimed in claim 1, wherein the head part comprises one or more apertures.

7. A laryngeal mask as claimed in claim 6, comprising two apertures.

8. A laryngeal mask as claimed in claim 6, wherein the apertures are generally eye-shaped.

9. A laryngeal mask as claimed in claim 6, wherein the apertures are positioned adjacent the resiliently deformable portion.

10. A laryngeal mask as claimed in claim 7, wherein the apertures are positioned opposite to one another in the enclosing wall of the head part.

11. A laryngeal mask as claimed in in claim 1, wherein the head part is generally tear-drop shaped.

12. A laryngeal mask as claimed in in claim 1, wherein the head part further comprises an epiglottic rest.

13. A laryngeal mask as claimed in in claim 1, wherein compression of the resiliently deformable portion reduces the distance between the sealing face and a part of the opposing face by between 13.5 mm and 16.5 mm.

14. A laryngeal mask as claimed in claim 1, wherein in the uncompressed configuration, the distance between the sealing face and a part of the opposing face is between 36 mm and 44 mm, and in the compressed configuration, said distance is between 22.5 mm and 27.5 mm.

15. A laryngeal mask as claimed in claim 14, wherein the mask comprises silicone.

* * * * *